US008784846B2

(12) United States Patent
Schulte et al.

(10) Patent No.: US 8,784,846 B2
(45) Date of Patent: Jul. 22, 2014

(54) SYSTEMS AND METHODS FOR PARTICLE RADIATION ENHANCED DELIVERY OF THERAPY

(75) Inventors: Reinhard Schulte, Grand Terrace, CA (US); Gilmer Valdes-Diaz, Hialeah, FL (US)

(73) Assignee: Loma Linda University Medical Center, Loma Linda, CA (US)

( * ) Notice: Subject to any disclaimer, the term of this patent is extended or adjusted under 35 U.S.C. 154(b) by 628 days.

(21) Appl. No.: 12/694,642

(22) Filed: Jan. 27, 2010

(65) Prior Publication Data

US 2011/0182806 A1 Jul. 28, 2011

Related U.S. Application Data

(63) Continuation of application No. PCT/US2008/071653, filed on Jul. 30, 2008.

(60) Provisional application No. 60/952,773, filed on Jul. 30, 2007.

(51) Int. Cl.
*A61K 51/00* (2006.01)
*A61K 49/00* (2006.01)
*A61K 9/00* (2006.01)
*A61K 9/14* (2006.01)

(52) U.S. Cl.
USPC ............ 424/400; 424/1.11; 424/9.1; 424/489

(58) Field of Classification Search
None
See application file for complete search history.

(56) References Cited

U.S. PATENT DOCUMENTS

| | | | |
|---|---|---|---|
| 5,440,133 A | 8/1995 | Moyers et al. | |
| 5,820,879 A * | 10/1998 | Fernandez et al. | 424/450 |
| 6,165,440 A * | 12/2000 | Esenaliev | 424/1.11 |
| 6,180,942 B1 | 1/2001 | Tracy et al. | |
| 6,818,199 B1 | 11/2004 | Hainfeld et al. | |
| 6,955,639 B2 | 10/2005 | Hainfeld et al. | |
| 7,763,544 B2 * | 7/2010 | Bai et al. | 438/704 |
| 2002/0064554 A1 * | 5/2002 | O'Brien et al. | 424/450 |
| 2003/0228260 A1 | 12/2003 | Filler | |
| 2005/0020869 A1 | 1/2005 | Hainfeld et al. | |
| 2005/0090732 A1 | 4/2005 | Ivkov et al. | |
| 2005/0276861 A1 | 12/2005 | Kipp et al. | |
| 2007/0009441 A1 | 1/2007 | Erathodiyil et al. | |
| 2009/0101846 A1 * | 4/2009 | Boyden et al. | 250/492.1 |

OTHER PUBLICATIONS

Stankovic, M., et al., "Properties of grape seed proanthocyanidins and quercetin in human lymphocytes" 2008, Arch. Biol. Sci., 60 (3), 367-377.*
Jo, Seong-Min et al., "Glucose-triggered release from liposomes incorporating poly(N-isopropylacrylamide-co-methacrylic-acid-co-octadecylacrylate) and glucose oxidase", Colloid Polym Sci., 2009, 287, pp. 379-384.*
Sadrozinski et al., Issues in Proton Computed Tomography, Nuclear Instruments and Methods in Physics Research A 511, 2003, pp. 275-281.
Schulte et al., Nanoparticle-Enhanced Proton Computed Tomography: A Monte Carlo Simulation Study, Biomedical Imaging: Nano to Macro, 2004, IEEE International Symposium, Apr. 15-18, 2004, p. 1354.
Laloup, Jennifer, "Cancer Therapy Without Side Effects Nearing Trials," dated Apr. 13, 2008 from http://www.wired.com/print/medtech/health/news/2008/04/kanzius_therapy on Apr. 23, 2008.
International Search Report and Written Opinion for Corresponding Application PCT/US08/71653.
Australian First Office Action, App No. 2008282215, dated Dec. 6, 2012.
Japanese Office Action, App. No. 2010-520162, dated Dec. 11, 2012.
European Supplementary Search Report, App No. EP 08 82 6721, Dated Oct. 24, 2012.
European Search Report dated Oct. 24, 2012 of corresponding European Patent Application No. 08826721.6.

* cited by examiner

*Primary Examiner* — Michael G Hartley
*Assistant Examiner* — Lance Rider
(74) *Attorney, Agent, or Firm* — Knobbe Martens Olson & Bear, LLP

(57) ABSTRACT

Systems and methods for enhancing the selective targeting of agents for preferential action at a target with reduced action with healthy tissue distal the target tissue. One or more agents can be combined with nano scale structures/particles for delivery to the target tissue. Appropriate bombardment with accelerated particle radiation, such as proton radiation, induces the release of the agents at the target site. Nano carriers can be combined with therapeutic and/or imaging enhancement agents. Imaging of the target tissue can provide a verification of the delivered dose of particle radiation. Nanocarriers can be provided with an outer shell selected for biocompatibility and durability in the in vivo environment and further selected to provide a feedback mechanism in the treatment environment to accelerate the release of the agent and reduce a total radiation dose needed for that release.

23 Claims, 5 Drawing Sheets

SYSTEMS AND METHODS FOR PARTICLE RADIATION ENHANCED DELIVERY OF THERAPY

CROSS-REFERENCE TO RELATED APPLICATIONS

This application is a U.S. National Phase of International Application No. PCT/US2008/071653, filed Jul. 30, 2008, which claims the benefit of U.S. Provisional Application 60/952,773, filed Jul. 30, 2007. This application hereby expressly incorporates by reference each of the above-identified applications in their entirety.

BACKGROUND OF THE INVENTION

1. Field of the Invention

The invention relates to the field of medical therapy and to systems and methods of enhancing delivery of therapeutic agents to targeted tissue via particle radiation bombardment and/or systems and methods for guiding delivery of particle radiation via post treatment imaging of the target tissue.

2. Description of the Related Art

Cancer remains one of the more challenging diseases to develop effective therapies for. One fundamental difficulty is the ability to effectively deliver cancer drug activity to the tumor while avoiding activity of the cancer drug on non-cancerous tissue. The ideal therapeutic drug would selectively reach the desired tumors target without negatively affecting non-cancerous tissue. However, existing regimens of chemotherapy and other targeted cancer therapies fall short of this ideal. For example, in some instances only between one to ten parts per one hundred thousand of intravenously administered monoclonal antibodies targeting cancer cells reach their intended targets.

Two main approaches or goals have been used recently to attempt to preferentially concentrate therapeutic agents at tumor sites. A first approach is to increase the targeting selectivity of cancer drugs. A second is to attempt to overcome biological barriers that inhibit cancer drugs from effectively reaching their intended targets, e.g. tumors.

Targeting mechanisms can be generally divided into two main groups: passive and active mechanisms. One well known passive targeting mechanism is referred to as enhanced permeation and retention (EPR). EPR exploits the physiological phenomenon that capillaries at the site of infection, inflammation and solid tumors often have a compromised barrier function, facilitating extravasation and protracted lodging of drug carriers. Thus, therapeutic agents with prolonged circulation times would be expected to be preferentially targeted to the tumor area with respect to non-cancerous tissue. However, depending on the surface characteristics of drug carriers, the carriers can be taken up by the reticuloendothelial system (RES) rather than the tumor tissue, resulting in relatively short circulation time. In general, carriers exhibiting hydrophobic surfaces tend to be absorbed by the RES cells of the liver and to a lesser degree by those of the spleen and lungs. Accordingly, a coating of hydrophilic compounds, such as polyethylene glycol (PEG) can reduce RES sequestration and significantly extend circulatory half life.

Active targeting mechanisms can include the molecular targeting of drug carriers by combining or conjugating the active recognition aspects of tumor specific molecules to the surfaces of drug carrier particles. For example, tumor specific antigens have been used to direct nano particles to angiogenic endothelium, for example to target $\alpha_v\beta_3$ integrins perfluorocarbon nano emulsions for MRI imaging of neovasculature and anti-angiogenesis therapy for melanoma and colon adenocarcinoma.

Another type of active, site directed drug delivery mechanism uses some form of external energy to direct the delivery of drug carriers. Examples of directed energies that have been used experimentally to control the pharmacokinetics and activation of cytotoxic drugs include magnetic fields, photonic radiation, heat, and ultrasound. For example, by applying a suitable magnetic field to specific regions of tissue, capsules loaded with magnetic materials can be driven preferentially to a tissue area. Another example of site directed targeting is induction of adhesion proteins in tumor microvasculature by ionizing radiation which is then used as antigenic targets for site specific drug delivery to tumor blood vessels. Other examples include the use of focused ultrasound to burst lipid encapsulated microbubbles and localized thermal ablation of cancer regions with near infrared photonic radiation.

However, a limitation of such directed energy mechanisms are that they exhibit poor tissue penetration and poor localization. For example, photonic radiation begins delivery energy to the surface of the tissue and the delivered energy tends to drop off exponentially with passage through the tissue. This can result in misdirected drug delivery due to the non-optimal dose profile of the radiation. Thus it will be understood that there exists a need for improved systems and methods of effectively targeting cancer drugs to cancer cells while reducing undesired effects on healthy tissue. There is also a need to more precisely identify cancerous tissue and confirm delivery of therapy thereto.

SUMMARY OF THE INVENTION

Embodiments are based at least in part on a realization of the advantages of accelerated particle radiation to enhance the regional specificity of therapy delivery. Protons and heavier positive ions exhibit the physical characteristics of delivering a significant portion of their initial energy at a predictable depth of penetration in the target tissue. This physical characteristic is referred to as the Bragg peak and differs significantly from the generally exponentially decreasing energy transfer profile exhibited by photonic radiation. By adjusting the initial velocity/energy of protons or other heavier positive ions, the associated Bragg peak can be selected to coincide with a desired depth of penetration at the desired target location, such as a cancerous tumor. By intentionally providing a range of initial velocities/energies, a spread out Bragg peak can be provided to substantially coincide with the extent of the target tissue.

By significantly reducing the amount of energy transfer to patient tissue between the surface and the target location as compared to photonic radiation, particle radiation, such as proton beam therapy, offers the advantage of providing an effective dose at the target site with significantly reduced undesired transfer of energy to presumably healthy tissue upstream of the target tissue. As a significant portion of the initial energy of proton radiation is deposited at the Bragg peak, particle radiation also offers the advantage of a significant reduction in downstream delivery of energy beyond the target tissue. Proton therapy is also well suited for a fractionated delivery regimen where a smaller fraction of a total dose can be delivered along a plurality of different spatial vectors to intersect at the desired target tissue. This aspect further reduces undesired transfer of radiation energy to upstream and downstream healthy tissue as the approach path for each therapy fraction can differ such that any given portion of healthy tissue sees at most a fraction of the total delivered therapeutic energy.

Embodiments are also based on a new understanding of the ability of particle radiation, such as accelerated proton and/or other heavy positive ion radiation, to induce the release of various types of treatment agents from carrier vehicles. For example, cancer drugs and/or other therapeutic agents can be combined with a nano scale structure or particle in such a way that they can be durably entrained within living tissue until they arrive at a desired target location. Appropriate bombardment with particle radiation can then induce the release and/or activation of the therapeutic agents in a concentrated manner at the target location. The previously described spread out Bragg peak can be employed to preferentially localize the activation/release of one or more therapeutic agents within the spread out Bragg peak region. An energy required to activate/release the therapeutic agents can be selected to define a threshold such that undesired activation/release of the agents outside the target tissue area is significantly reduced. Embodiments also employ the particle radiation induced release/activation of imaging enhancement agents and subsequent imaging of the target tissue to verify delivered doses of the radiation.

One embodiment includes a method of delivering therapy, the method comprising introducing a quantity of therapeutic agent into a patient and directing a dose of particle radiation at target tissue of the patient so as to preferentially induce action of the therapeutic agent proximal the target tissue with respect to distal the target tissue.

Another embodiment includes an in vivo agent delivery vehicle comprising a nanostructure and in vivo agent engaged with the nanostructure such that the in vivo agent can be durably entrained within living tissue and wherein bombardment with a selected dose of particle radiation releases the in vivo agent from the nanostructure.

A further embodiment includes a method of image guided radiation therapy, the method comprising introducing a quantity of imaging enhancement agent into a patient, directing a dose of particle radiation at target tissue of the patient so as to preferentially induce action of the imaging enhancement agent proximal the target tissue with respect to distal the target tissue, imaging the target tissue, and verifying the dose of particle radiation delivered to the target tissue by analyzing a degree of enhancement of the target tissue image as compared to an image of non-target tissue adjacent the target tissue.

DETAILED DESCRIPTION OF THE PREFERRED EMBODIMENT

Figure 1:
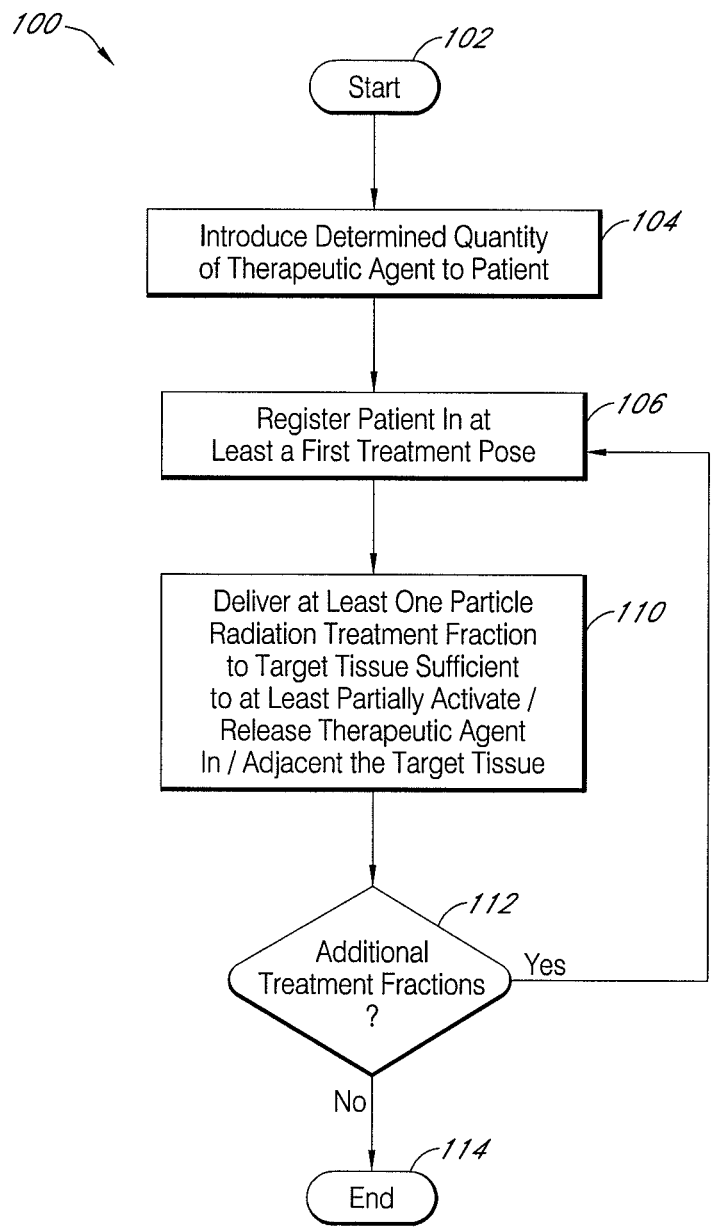
FIG. 1 is a flowchart of embodiments of a method of enhancing delivery of therapeutic agents with particle radiation.

FIG. 1 is a flowchart illustrating methods 100 of enhancing delivery of therapeutic agents with particle radiation. The method 100 begins in a start block 102. The start block 102 can include the preparatory analysis and diagnosis of a patient's condition by an attending clinician and determining an appropriate therapy regimen. For example, the block 102 can include selecting an appropriate cancer drug and an appropriate fractionated proton therapy prescription. The particular appropriate drugs, doses, radiation energies, approach vectors, and the like can vary widely depending on the particular disease state and patient condition, however, the particular prescription for a given patient and condition will be readily determined by one of ordinary skill.

Following in a block 104, a determined quantity of therapeutic agent is introduced to the patient. The particular method of introduction of the therapeutic agent can depend on the particular type of agent to be introduced and the location of the target tissue, however in various implementations can include one or more of intravenous delivery, transdermal delivery, oral administration, a nebulizer, and the like.

In some embodiments, introduction of the therapeutic agent in block 104 can comprise introduction of an agent delivery vehicle 200 described and illustrated in greater detail below with respect to FIGS. 2 and 3. In some embodiments, an agent delivery vehicle 200 comprises a nano scale structure or particle. A nano scale particle structure in some embodiments comprises structures or particles having a major dimension x less than approximately 100 nm. In some embodiments, a nano scale delivery vehicle 200 preferably has a mean major dimension of approximately 50 nm. It will be understood that the particular dimensions of individual delivery vehicles 200 can vary and the preferred mean size can vary, depending on the composition of the delivery vehicle and any therapeutic agent(s) combined therewith. It will thus be understood that the values and ranges described herein are simply exemplary and other sizes and ranges are possible.

Following the introduction of the therapeutic agent in block 104 and allowing sufficient time for the therapeutic agent to diffuse through or otherwise arrive at the desired target tissue, a block 204 is implemented to register the patient in at least a first treatment pose. Registering the patient refers to a process and system for orienting and maintaining a patient at a given translational and rotational orientation with respect to a particle radiation delivery assembly such that a given treatment fraction arrives at the target tissue along a desired spatial vector. As previously noted, the Bragg peak generally occurs after the particle radiation has passed through a given depth of patient tissue and thus it will generally be indicated that particle radiation be directed not only at a selected target iso center but also along a selected approach vector such that the Bragg peak of the radiation beam coincides with the target tissue rather than upstream or downstream therefrom. Additional detailed description and illustration of the registration process of block 106 will be provided below with a more detailed description of an exemplary suitable radiation therapy system 400 as illustrated and described below in greater detail with respect to FIGS. 5A and 5B.

Once the patient has been properly registered for the given treatment fraction in block 106, a block 110 follows wherein one or more particle radiation treatment fractions are directed towards the target tissue. The delivered dose is selected to at least partially activate and/or release the therapeutic agent in and/or adjacent to the target tissue. Therapeutic particle radiation can be characterized according to the amount of energy transferred per unit path length of the particle that does the energy transfer. Heavy ion accelerated particles generally exhibit what is considered a high linear energy transfer (LET)

of greater than approximately 10 keV/μm to more than 100,000 keV/μm. Low LET accelerated particles are generally characterized by an LET not exceeding a few keV/μm. Accelerated protons are generally between low LET photons and relatively high LET heavy ions. In some embodiments, protons exhibit the characteristic that the entrance or plateau region of the beam exhibits a low LET and the LET rises up to about 80 keV/μm in the Bragg peak. As previously described, some embodiments employ a spread out Bragg peak such that the LET is a mixture and covers a range from low to high LET values. In general, particles having a higher LET will exhibit a larger effect on nano scale particles and structures due to the more concentrated release of energy over short distances.

Following the treatment fraction delivered in block 110, a decision is made in a block 112 whether additional treatment fractions are indicated. In some embodiments, delivery of particle radiation need not be fractionated and only a single dose of particle radiation can be delivered at a given treatment session. For at least some patients, a single non-fractionated treatment dose of approximately 20 to 25 Gray (Gy) would comprise an appropriate radiation dose. In some embodiments, a treatment fraction of a smaller dose, such as approximately 2 Gy can be delivered per treatment fraction. In general, in such a fractionated treatment regimen, the patient can be repositioned and re-registered and a further treatment fraction administered via iterations of blocks 106 and 110. However, it will be understood that the patient need not be moved with respect to the particle radiation delivery assembly for each fraction and that multiple fractions can be delivered along a given pose.

Figure 2:
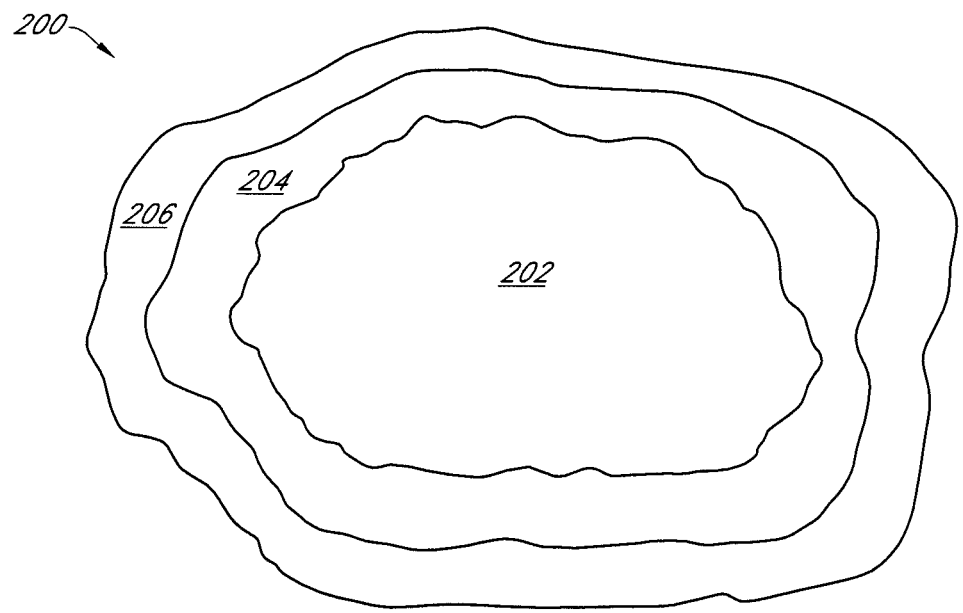
FIG. 2 is a schematic section view of embodiments of a delivery carrier/vehicle for conveying an in vivo agent to a target site.
Figure 3:
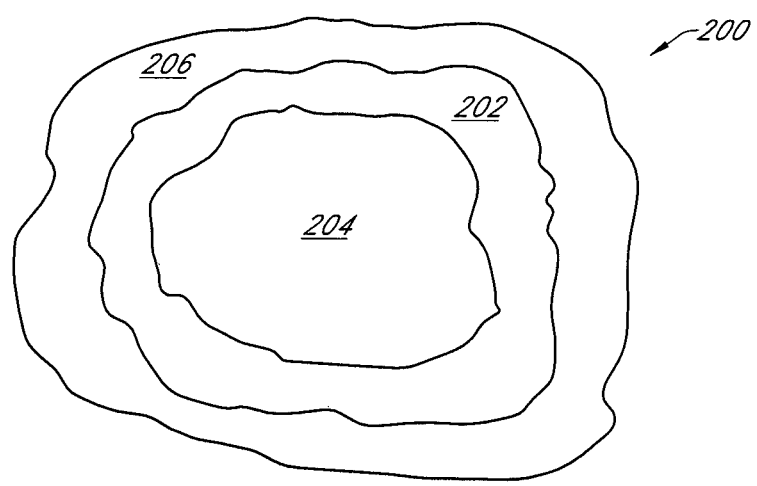
FIG. 3 is a schematic section view of additional embodiments of a delivery carrier/vehicle for conveying an in vivo agent to a target site.

FIGS. 2 and 3 illustrate in greater detail a schematic sectional illustration of embodiments of an agent delivery vehicle 200. In the embodiments illustrated by FIG. 2, the delivery vehicle 200 comprises a nano structure 202. The nano structure 202 is generally a nano scale body and can be substantially solid or can exhibit one or more internal pores or voids. The nano structure 202 preferably comprises a biocompatible material. The nano structure 202 also preferably comprises a relatively high Z material. Relatively high Z materials exhibit the desirable characteristic of favorable interaction with the particle radiation bombardment. In some embodiments, the nano structure 202 comprises gold. Gold exhibits a useful release of secondary low energy electrons upon bombardment with a proton beam to facilitate release and activation of components engaged with the gold nano structure. In other embodiments, the nano structure 202 comprises platinum, however other elemental compositions and compounds for the nano structure 202 are possible.

The delivery vehicle 200 also comprises one or more in vivo agents engaged with the nano structure such that they can be entrained to the target tissue. In some embodiments, the agent 204 comprises a therapeutic agent, such as one or more cancer drugs. In some embodiments, the agent comprises a contrast media to enhance an image of imaged tissue where the contrast media is released/activated. In some embodiments, the agent comprises one or more radionuclides. The radionuclides can be selected to emit positrons when activated/released to enhance an image of imaged tissue containing the radionuclides. In some embodiments, the agent 204 can comprise one or more antibodies. For example, antibodies can be selected for particular tumor antigens.

In some embodiments, the delivery vehicle 200 further comprises an outer coating 206. The outer coating 206 is selected to enhance biocompatibility and preferential action of the delivery vehicle 200 at the target tissue location. Thus, in some embodiments, the outer layer 206 acts as a protective shell for the delivery vehicle 200 and the delivery vehicle 200 exhibits a multi-layer or nested core/shell configuration.

In some embodiments, the delivery vehicle 200 can be manufactured by the layer by layer apposition of oppositely charged macro molecules on colloidal templates. The delivery vehicles 200 can further comprise additional layered materials to provide a desired thickness, permeability, biostability and biocompatibility including but not limited to synthetic poly electrolytes, natural polymers such as polysaccharides, polypeptides and/or polynucleotides, lipids, and/or multi-valent imaging agents. In some embodiments, the delivery vehicle 200 is formed at least in part with covalent bonding. The incident particle radiation is ionizing with sufficient energy to break the covalent bonding either directly or via indirect action of radiation induced radicals. In some embodiments, the outer layer 206 is selected of organic and/or inorganic material such that bombardment with particle radiation degrades the outer layer 206 thereby exposing and releasing the agent layer 204.

In some embodiments, the delivery vehicle 200 can employ biological feedback processes in combination with particle radiation bombardment to facilitate degradation of the outer layer 206 or otherwise release/activate the agent 204 from the nano structure 202. In some embodiments, the outer layer 206 comprises a hydrogel and one or more selected enzymes. Upon bombardment with particle radiation, at least a portion of the enzymes are released from the hydrogel in the outer shell 206. The release of enzymes from the outer shell 206 can involve a small number of enzyme molecules, including only a single enzyme molecule. The released enzyme molecules react with target molecules in the in vivo environment, for example glucose. The enzymes can react with the cellular environment to produce a change in one or more characteristics, preferably in a generally localized manner. In some embodiments, the enzymes can react with the cellular environment to produce an acidic reaction product, thereby lowering the local pH. In some embodiments, lowering the local pH will induce release of further enzyme molecules from the outer layer 206 thereby leading to a feedback or chain reaction facilitating more rapid release/activation of the payload or agent 204 from the delivery vehicle 200.

In some embodiments, feedback or trigger mechanisms provided by the outer layer 206 in combination with particle radiation bombardment can specifically target tumor tissue. In some embodiments, bombardment with particle radiation up regulates production of certain proteins in cancerous tumors and/or tumor vasculature. Enzymes in the outer layer 206 can be selected to be substrate specific for the up regulated proteins and can catalyze a reaction leading to a lower localized pH. Such embodiments are preferred as the effects of the localized release of the agents 204 is more specifically selective for the tumor cells with respect to normal healthy cells adjacent the tumor cells in the target tissue. These embodiments can provide particular advantages when the tumor cells do not define a continuous mass but instead are interspersed with healthy tissue that is preferably spared exposure to the agent 204.

FIG. 3 illustrates a schematic section view of an alternative structure of delivery vehicle 200. Certain structures, compositions, and features of the delivery vehicle as illustrated with respect to FIG. 3 share substantial similarities with the embodiments of delivery vehicle 200 previously illustrated and described with respect to FIG. 2 and such similarities will not be repeated for brevity and ease of understanding. The primary difference in the embodiments of delivery vehicle 200 in FIG. 2 with respect to FIG. 3 is that the embodiments of FIG. 3 substantially enclose the agent 204 in an interior of the nano structure 202 rather than about an exterior as in FIG. 2. In some embodiments, the nano structure 202 comprises a porous structure such that the agent 204 resides within one or more pores or voids of the nano structure 202. In other embodiments, the nano structure 202 comprises a shell that can be either solid or can comprise a mesh form. Upon bombardment with a selected dose of particle radiation, such a hollow shell or mesh configuration of nano structure opens or ruptures to release the agent 204.

One additional similarity between the embodiments of delivery vehicle 200 illustrated in FIGS. 2 and 3 is that individual delivery vehicles 200 can have an irregular form. In some embodiments, the delivery vehicles 200 can be generally spherical, however a wide variety of other regular and irregular shapes are possible. It will further be understood that in many implementations, a large plurality of delivery vehicles 200 will be introduced into the patient and thus will in such embodiments exhibit a range of sizes and shapes. However, as previously noted in some embodiments a major dimension x of approximately 100 nm or less is generally preferred and in some embodiments a mean major dimension of approximately 50 nm is more preferred. A size of approximately 50 nm is, in at least some implementations, a preferred size for uptake into cells but this is not required to achieve significant advantages and benefits of the various embodiments described herein.

It will be understood that in some embodiments, a plurality of agents 204 can be combined in the delivery vehicles 200. For example, the delivery vehicles 200 can be manufactured to offer combined drug treatment therapies. In one non-limiting example, radiosensitizing drugs such as 5-Fluorouracil and Cisplatin can be combined with biologically active drugs such as EGF and PDGF receptor inhibitors. For example, the PDGF receptor kinase inhibitor Imatinib can decrease interstitial fluid pressure in tumors, leading to a tumor specific increase in the uptake of concomitantly delivered drugs.

Figure 4:
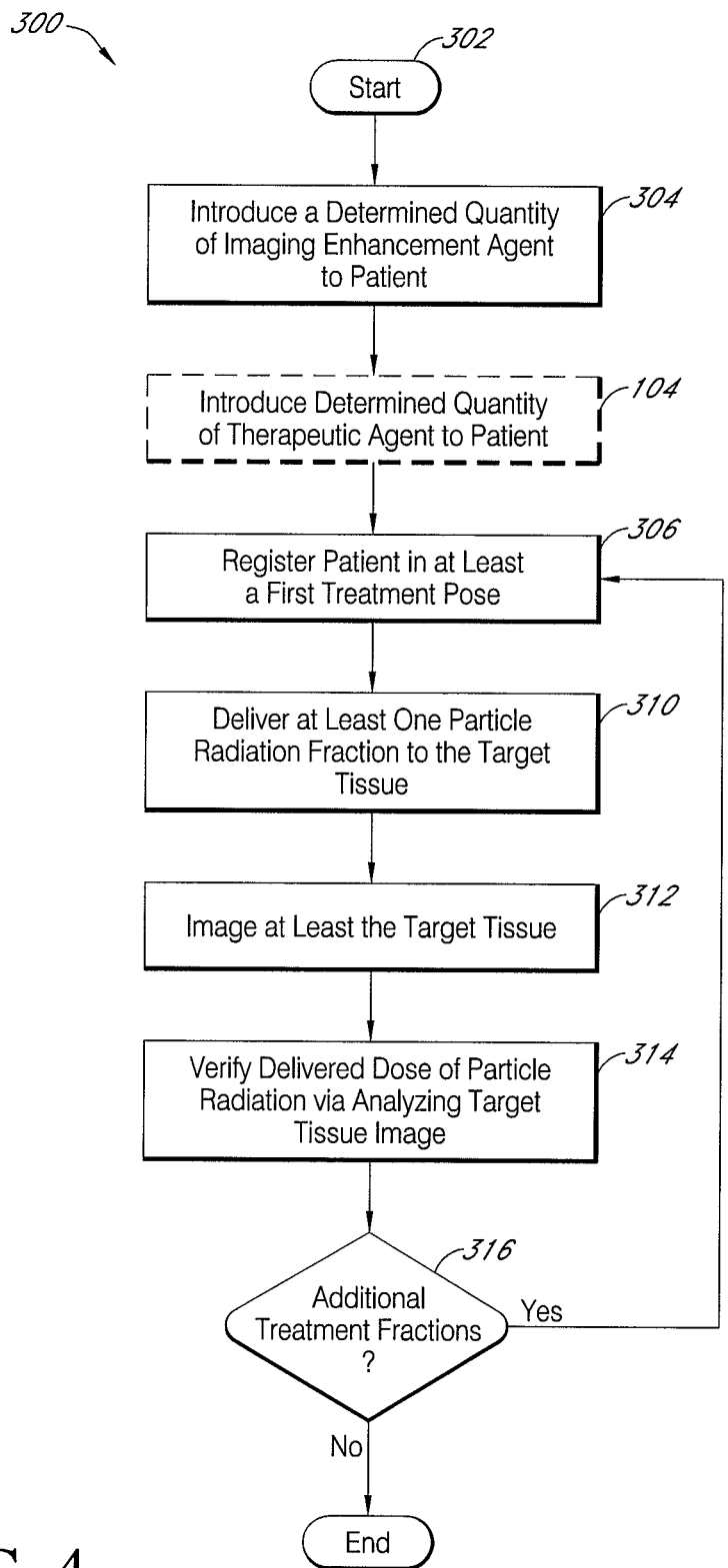
FIG. 4 is a flowchart of embodiments of a method of enhancing imaging with particle radiation to facilitate more accurate delivery of therapy.

FIG. 4 illustrates embodiments that can be implemented in combination with or as an alternative to the embodiments previously described with respect to FIG. 1. FIG. 4 is a flowchart illustrating embodiments of a method for image guided radiation therapy 300 or method 300 for brevity. The method 300 begins in a start block 302 which generally includes diagnosis and determination of an appropriate treatment regimen for the patient in a similar manner to that previously described with respect to the block 102.

In a block 304, a determined quantity of imaging enhancement agent is introduced to the patient, in some embodiments via entrainment with the delivery vehicles 200. As previously noted, in some embodiments the agent 204 can comprise one or more therapeutic agents. In some embodiments, the agent 204 can comprise in addition to or as an alternative to therapeutic agents, one or more image enhancement agents adapted to facilitate or enhance an image of selected tissue. In some embodiments, the agent 204 comprises contrast media which when released or activated increase the effective imaging density of the associated tissue. In one embodiment, contrast media comprising the agent 204 can comprise a plurality of small gold nano particles that are released upon bombardment with particle radiation. In some embodiments, the agent 204 can comprise one or more positron emitting radionuclides that can be imaged with a combination of PET and CT. For relatively small sizes of delivery vehicle 200, for example in the nano scale dimension, the number of incident protons intercepting them will be generally randomly distributed according to a Poisson distribution. If the dose concentration is selected sufficiently small such that only a fraction of nano scale delivery vehicles 200 are intercepted, the number of delivery vehicles affected will increase generally linearly with delivered dose.

As previously noted, the method 300 can be implemented in combination with the method 100 previously described. Thus, an optional block 104 can be implemented substantially similarly to that previously described with respect to the method 100.

In a block 306, the patient is registered in at least a first desired treatment pose in a similar manner to that previously described with respect to block 106. In a block 310, at least one particle radiation treatment fraction is delivered to the target tissue, again in a similar manner to that previously described with respect to block 110.

In a block 312, at least one image is obtained of the target tissue and the image can include adjacent non-target tissue. A wide variety of imaging systems and methodologies are available that can be advantageously implemented with embodiments as described herein and the choice of an appropriate imaging system and methodology will be readily apparent to one of ordinary skill.

In a block 314, the delivered dose of particle radiation can be verified via analyzing the image data from block 312. For example, contrast media and/or positron emitting radionuclides comprising the agent 204 will be activated/released by the particle radiation provided in block 310 and will provide an enhanced image in block 312 with respect to adjacent tissue where the image enhancement agent 204 was to a significantly lesser degree activated/released. The relative degree of enhancement determined in block 314 provides an independent verification of the dose of particle radiation actually delivered to the target tissue providing a valuable verification function.

As previously noted, a radiation treatment regimen can be fractionated and in some implementations a decision is made in a block 316 whether additional treatment fractions are indicated. If so, the patient can be re-registered in an iteration of block 306 and additional treatment fractions delivered in iterations of block 310. If the final treatment fraction has been delivered or in embodiments including non-fractionated treatment delivery, the method 300 would then end.

In some embodiments, the delivery vehicles 200 can comprise materials selected for direction specifically against tumors. For example, in some embodiments the delivery vehicles 200 can comprise antibodies selected against tumor antigens. Directed release via bombardment with particle radiation of the antibodies adjacent the tumors rather than relying on tumor finding properties of systemically injected antibodies results in more effective targeting of tumors with the antigen seeking antibodies in these embodiments. In some embodiments, the agent 204 comprises antibodies associated with one or more photon and/or positron emitting radionuclides. The agent 204 can thus specifically target tumors and provide an enhanced imaging of tumor nodules within organ tissue affected by the tumor.

For example, early stage prostate cancer may exhibit a single or small number of microscopic cancer foci within an organ volume that is otherwise generally free of cancer. SPECT imaging with Capromab Pentetide, and In-labeled antibody against prostate specific membrane antigen (PSMA), a glycoprotein that is up regulated and prostate adenocarcinoma can provide highly specific enhanced imaging of the cancer foci and facilitate even more specific targeting of the particle radiation to the cancer foci while reducing targeting as much as possible healthy non-cancerous tissue within the organ volume.

Figure 5A:
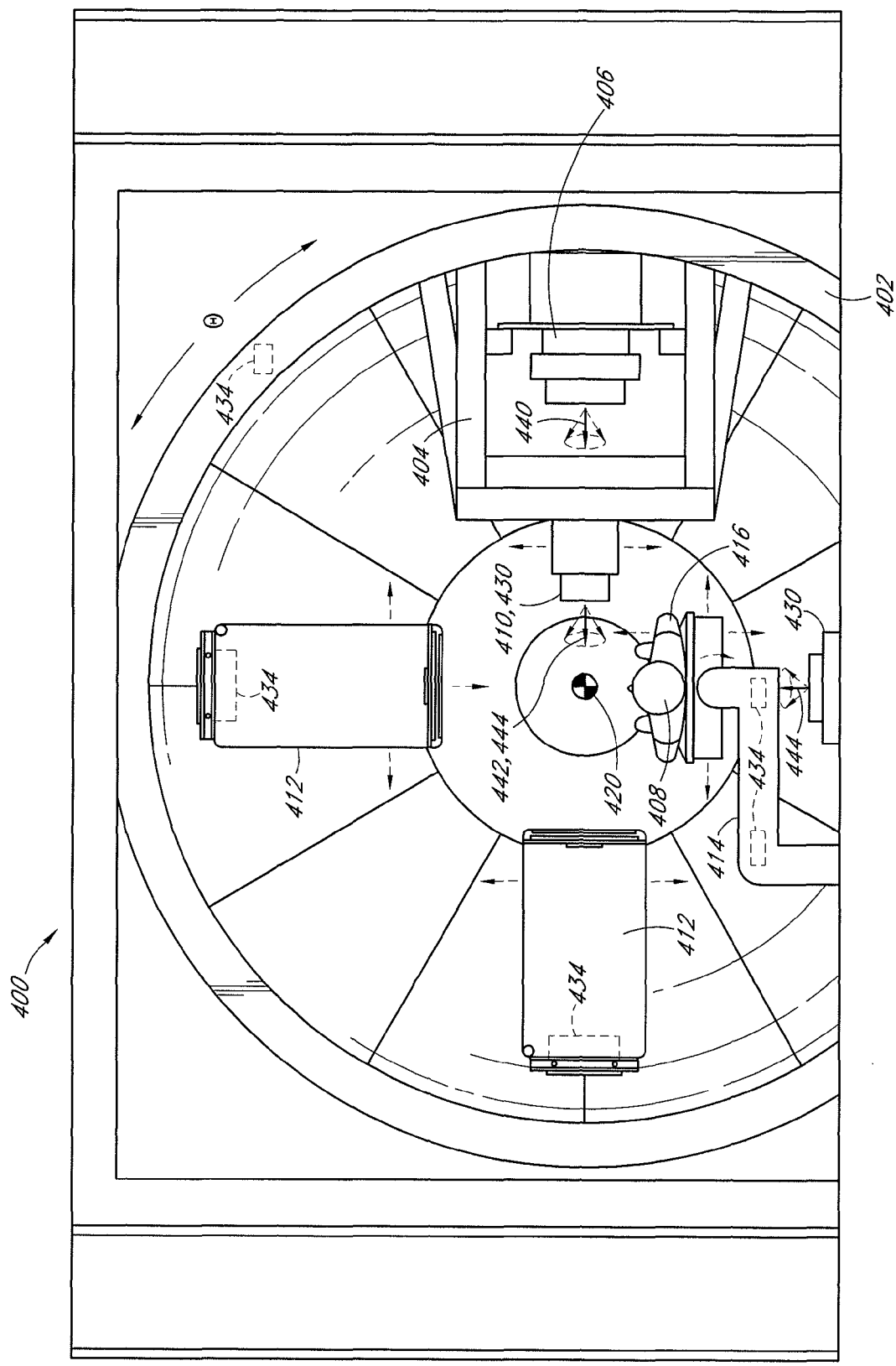
FIGS. 5A and 5B are schematic illustrations of embodiments of a particle therapy delivery system.
Figure 5B:
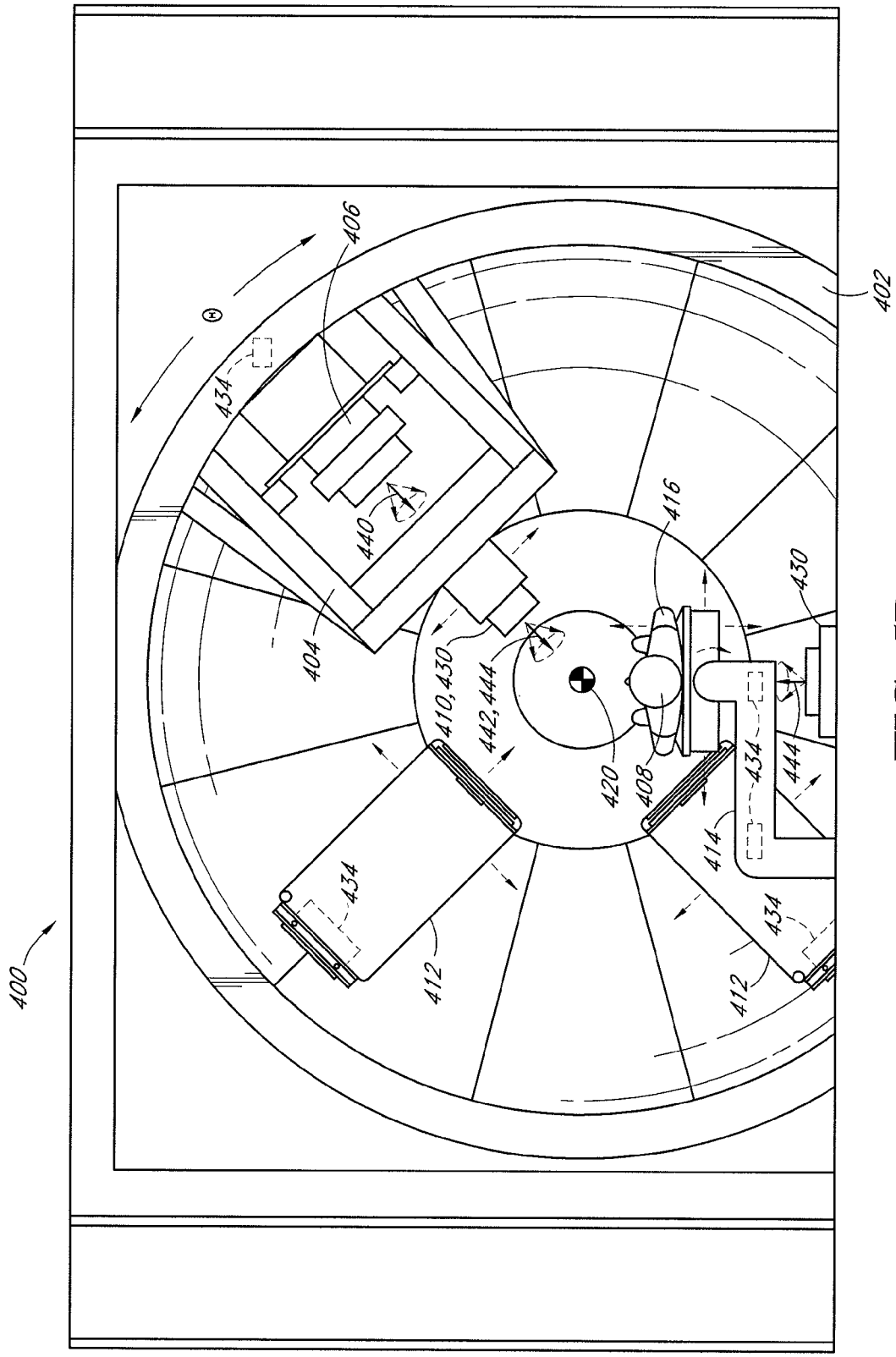

FIGS. 5A and 5B illustrate schematically first and second orientations of one embodiment of a particle radiation therapy system 400, such as based on the proton therapy system currently in use at Loma Linda University Medical Center in Loma Linda, Calif. and as described in U.S. Pat. No. 4,870,287 of Sep. 26, 1989 which is incorporated herein in its entirety by reference. The radiation therapy system 400 is designed to deliver therapeutic radiation doses to a target region within a patient for treatment of malignancies or other conditions from one or more angles or orientations with respect to the patient. The system 400 includes a gantry 402 which includes a generally hemispherical or frustoconical support frame for attachment and support of other components of the radiation therapy system 400. Additional details on the structure and operation of embodiments of the gantry 402 may be found in U.S. Pat. Nos. 4,917,344 and 5,039,057, both of which are incorporated herein in their entirety by reference.

The system 400 also comprises a nozzle 404 which is attached and supported by the gantry 402 such that the gantry 402 and nozzle 404 may revolve relatively precisely about a gantry iso center 420. The system 400 also comprises a radiation source 406 delivering a radiation beam along a radiation beam axis 440, such as a beam of accelerated protons. The radiation beam passes through and is shaped by an aperture 410 to define a therapeutic beam delivered along a delivery axis 442. The aperture 410 is positioned on the distal end of the nozzle 404 and the aperture 410 may preferably be specifically configured for a patient's particular prescription of therapeutic radiation therapy. In certain applications, multiple apertures 410 are provided for different treatment fractions.

The system 400 also comprises one or more imagers 412 which, in this embodiment, are retractable with respect to the gantry 402 between an extended position and a retracted position. The imager 412 in one implementation comprises a commercially available solid-state amorphous silicon x-ray imager which can develop image information such as from incident x-ray radiation that has passed through a patient's body. The retractable aspect of the imager 412 provides the advantage of withdrawing the imager screen from the delivery axis 442 of the radiation source 406 when the imager 412 is not needed thereby providing additional clearance within the gantry 402 enclosure as well as placing the imager 412 out of the path of potentially harmful emissions from the radiation source 406 thereby reducing the need for shielding to be provided to the imager 412.

The system 400 also comprises corresponding one or more x-ray sources 430 which selectively emit appropriate x-ray radiation along one or more x-ray source axes 444 so as to pass through interposed patient tissue to generate a radiographic image of the interposed materials via the imager 412. The particular energy, dose, duration, and other exposure parameters preferably employed by the x-ray source(s) 430 for imaging and the radiation source 406 for therapy will vary in different applications and will be readily understood and determined by one of ordinary skill in the art.

In this embodiment, at least one of the x-ray sources 430 is positionable such that the x-ray source axis 444 can be positioned so as to be nominally coincident with the delivery axis 442. This embodiment provides the advantage of developing a patient image for registration from a perspective which is nominally identical to a treatment perspective. This embodiment also includes the aspect that a first imager 412 and x-ray source 430 pair and a second imager 412 and x-ray source 430 pair are arranged substantially orthogonal to each other. This embodiment provides the advantage of being able to obtain patient images in two orthogonal perspectives to increase registration accuracy as will be described in greater detail below. The imaging system can be similar to the systems described in U.S. Pat. Nos. 5,825,845 and 5,117,829 which are hereby incorporated by reference.

The system 400 also comprises a patient positioner 414 and a patient pod 416 which is attached to a distal or working end of the patient positioner 414. The patient positioner 414 is adapted to, upon receipt of appropriate movement commands, position the patient pod 416 in multiple translational and rotational axes and preferably is capable of positioning the patient pod 416 in three orthogonal translational axes as well as three orthogonal rotational axes so as to provide a full six degree freedom of motion to placement of the patient pod 416.

The patient pod 416 is configured to hold a patient securely in place in the patient pod 416 so to as substantially inhibit any relative movement of the patient with respect to the patient pod 416. In various embodiments, the patient pod 416 comprises expandable foam, bite blocks, and/or fitted facemasks as immobilizing devices and/or materials. The patient pod 416 is also preferably configured to reduce difficulties encountered when a treatment fraction indicates delivery at an edge or transition region of the patient pod 416.

Although the preferred embodiments of the present invention have shown, described and pointed out the fundamental novel features of the invention as applied to those embodiments, it will be understood that various omissions, substitutions and changes in the form of the detail of the device illustrated may be made by those skilled in the art without departing from the spirit of the present invention. Consequently, the scope of the invention should not be limited to the foregoing description but is to be defined by the appended claims.

What is claimed is:

1. A method of delivering therapy, the method comprising:
introducing a quantity of therapeutic agent into a patient, the therapeutic agent configured to provide a beneficial effect to the patient when allowed to appropriately interact with a target tissue;
introducing a quantity of protective agent into the patient, the protective agent configured to prevent the therapeutic agent from interacting with surrounding tissue;
introducing a quantity of activating agent into the patient, the activating agent having a high molecular weight and configured to be irradiated by particle radiation, thereby facilitating release of the therapeutic agent from the protective agent into the target tissue;
wherein the therapeutic agent, the protective agent, and the activating agent are associated with each other in the patient; and
directing a dose of particle radiation comprising accelerated protons or accelerated heavier positive ions having a Bragg peak at the target tissue of the patient so that the dose interacts with the activating agent proximal to the target tissue, thereby releasing the therapeutic agent from its association with the protective agent;
wherein the patient is oriented and the dose of particle radiation is directed into the patient at a specified vector so that the Bragg peak of the dose of particle radiation at least partially overlaps the activating agent proximal to the target tissue, thereby reducing undesired radiation to, and interaction of therapeutic agent with, non-target tissue.

2. The method of claim 1, wherein introducing the quantity of therapeutic agent comprises introducing a quantity of nanoparticle carriers combined with the therapeutic agent and wherein the nanoparticle carriers convey the therapeutic agent to the target tissue.

3. The method of claim 2, wherein irradiation with the particle radiation induces release of the therapeutic agent from the nanoparticle carriers.

4. The method of claim 3, wherein the nanoparticle carriers comprise at least one outer coating and wherein the irradiation with the particle radiation induces decomposition of the outer coating so as induce the release of the therapeutic agent from the nanoparticle carriers.

5. The method of claim 4, wherein the decomposition of the outer coating via the irradiation with the particle radiation induces a localized change in physical characteristics of the target tissue and wherein the changed physical characteristics of the target tissue accelerate the decomposition of the outer coating and the release of the therapeutic agent.

6. The method of claim 5, wherein the change in physical characteristics comprises a localized change in pH.

7. The method of claim 1, wherein the directing the dose of particle radiation comprises directing a dose of accelerated protons.

8. The method of claim 1, further comprising configuring the dose of particle radiation such that energy of the dose of particle radiation is preferentially deposited within the target tissue with respect to upstream and downstream of the target tissue such that the particle radiation provides therapy independently of the action of the therapeutic agent.

9. The method of claim 1, further comprising registering the patient such that the dose of particle radiation is directed along one or more desired treatment vectors to the target tissue.

10. The method of claim 1, further comprising:
introducing a quantity of imaging enhancement agent into the patient, the imaging enhancement agent configured to enhance the imaging of the patient after introduction; and
imaging the patient during and/or following the directing of particle radiation at the patient,
wherein the imaging enhancement agent is configured such that an image of the target tissue is responsive to the irradiation with particle radiation as a function of the delivered dose of the particle radiation such that the delivered dose can be verified via analyzing the imaging of the patient.

11. The method of claim 10, comprising forming the imaging enhancement agent by combining contrast nanoparticles with a nanocarrier such that the contrast nanoparticles are released from the nanocarrier upon bombardment with the particle radiation.

12. The method of claim 10, comprising forming the imaging enhancement agent by combining one or more positron emitting radionuclides with a nanocarrier such that the one or more positron emitting radionuclides are released from the nanocarrier upon bombardment with the particle radiation such that the one or more positron emitting radionuclides can be imaged.

13. The method of claim 12, further comprising forming the imaging enhancement agent by combining the one or more positron emitting radionuclides with antibodies selected for tumor antigens such that the antibodies preferentially select cancer foci within the target tissue and such that one or more positron emitting radionuclides enhance the image of the cancer foci with respect to non-cancerous tissue within the target tissue.

14. The method of claim 2, further comprising:
providing an in vivo agent delivery vehicle comprising the nanoparticle carriers; and
engaging the therapeutic agent with the nanoparticle carriers such that the therapeutic agent can be durably entrained within living tissue and wherein bombardment with a selected dose of particle radiation releases the therapeutic agent from the nanoparticle carriers.

15. The method of claim 14, wherein the therapeutic agent comprises a layer arranged about an exterior of the nanoparticle carriers.

16. The method of claim 15, further comprising an outer coating such that the therapeutic agent layer is interposed between the nanoparticle carriers and the outer coating.

17. The method of claim 14, wherein the nanoparticle carriers comprise one or more internal voids and wherein the therapeutic agent is contained at least partially within the one or more voids.

18. The method of claim 14, wherein the therapeutic agent comprises an in vivo agent that comprises antibodies selected for tumor antigens.

19. The method of claim 10, wherein the quantity of imaging enhancement agent is selected such that the degree of enhancement of the target tissue image is a generally linear function of the delivered dose of particle radiation.

20. The method of claim 10, further comprising selecting the image enhancement agent such that the imaging enhancement agent preferentially concentrates at the target tissue.

21. The method of claim 11, wherein releasing the nanoparticles increases the density of the target tissue.

22. The method of claim 3, wherein the activating agent comprises the nanoparticle carriers.

23. A method of delivering therapy, the method comprising:
introducing a quantity of therapeutic agent into a patient, the therapeutic agent configured to provide a beneficial effect to the patient when allowed to appropriately interact with a target tissue;
introducing a quantity of protective agent into the patient, the protective agent configured to prevent the therapeutic agent from interacting with surrounding tissue;
wherein the therapeutic agent and the protective agent are associated with each other in the patient; and
directing a dose of particle radiation comprising accelerated protons or accelerated heavier positive ions having a Bragg peak at the target tissue of the patient so that the dose interacts with the protective agent proximal to the target tissue, thereby releasing the therapeutic agent from its association with the protective agent;
wherein the patient is oriented and the dose of particle radiation is directed into the patient at a specified vector so that the Bragg peak of the dose of particle radiation at least partially overlaps the protective agent proximal to the target tissue, thereby reducing undesired radiation to, and interaction of therapeutic agent with, non-target tissue.

* * * * *